(12) United States Patent
Mazuir et al.

(10) Patent No.: US 10,024,504 B2
(45) Date of Patent: Jul. 17, 2018

(54) PREOPERATIVE LIGHTING DEVICE (71) Applicant: SOCIETE POUR LA CONCEPTION DES APPLICATIONS DES TECHNIQUES ELECTRONIQUES, Merignac (FR)

(72) Inventors: Alain Mazuir, Saint Maximin la Sainte Beaume (FR); Francis Dieras, Bordeaux (FR); Pascal Regere, Blanquefort (FR)

(73) Assignee: SOCIETE POUR LA CONCEPTION DES APPLICATIONS DES TECHNIQUES ELECTRONIQUES, Merignac (FR)

( * ) Notice: Subject to any disclaimer, the term of this patent is extended or adjusted under 35 U.S.C. 154(b) by 482 days.

(21) Appl. No.: 14/413,180

(22) PCT Filed: Jul. 4, 2013

(86) PCT No.: PCT/FR2013/051589
§ 371 (c)(1),
(2) Date: Jan. 6, 2015

(87) PCT Pub. No.: WO2014/006337
PCT Pub. Date: Jan. 9, 2014

(65) Prior Publication Data
US 2015/0167908 A1    Jun. 18, 2015

(30) Foreign Application Priority Data

Jul. 6, 2012 (FR) ...................................... 12 56555

(51) Int. Cl.
*F21K 99/00* (2016.01)
*A61B 5/00* (2006.01)
(Continued)

(52) U.S. Cl.
CPC .............. *F21K 9/56* (2013.01); *A61B 5/0071* (2013.01); *A61B 5/0088* (2013.01); *A61C 1/088* (2013.01);
(Continued)

(58) Field of Classification Search
CPC . F21K 9/56; F21K 9/64; A61B 5/0071; A61B 5/0088; A61B 1/043; A61B 1/0638;
(Continued)

(56) References Cited

U.S. PATENT DOCUMENTS

| 6,386,866 B1 | 5/2002 | Hecht et al. |
| 2006/0152926 A1 | 7/2006 | Hama et al. |

(Continued)

FOREIGN PATENT DOCUMENTS

| DE | 202004001189 U1 | 8/2004 |
| EP | 1269909 A1 | 1/2003 |

(Continued)

OTHER PUBLICATIONS

International Search Report for corresponding International Application No. PCT/FR2013/051589, dated Sep. 12, 2013.
(Continued)

*Primary Examiner* — Nicholas Lucchesi
(74) *Attorney, Agent, or Firm* — Workman Nydegger (57) ABSTRACT

A dental lighting device and process for using the same comprises at least one lighting system configured to light a predetermined dental zone with, over a first spectral range which is less than a reference wavelength between 405 nm and 475 nm, a first irradiance value E1 and, over a second spectral range greater than this reference wavelength, a second irradiance value E2, which lighting system is configured to function according to at least one first lighting mode in which the ratio of the first irradiance value E1 to the second irradiance value E2 is less than 12.

16 Claims, 3 Drawing Sheets (51) Int. Cl.
  *A61C 1/08* (2006.01)
  *F21V 23/04* (2006.01)
  *F21V 33/00* (2006.01)
  *F21K 9/64* (2016.01)
  *A61B 1/04* (2006.01)
  *A61B 1/06* (2006.01)
  *A61B 1/24* (2006.01)
  *F21W 131/202* (2006.01)
  *F21Y 115/10* (2016.01)
  *F21Y 113/13* (2016.01)

(52) U.S. Cl.
  CPC ........... *F21K 9/64* (2016.08); *F21V 23/04* (2013.01); *F21V 33/0068* (2013.01); *A61B 1/043* (2013.01); *A61B 1/0638* (2013.01); *A61B 1/24* (2013.01); *F21W 2131/202* (2013.01); *F21Y 2113/13* (2016.08); *F21Y 2115/10* (2016.08)

(58) Field of Classification Search
  CPC ........... A61B 1/24; A61C 1/088; F21V 23/04; F21V 33/0068; F21Y 2113/13; F21Y 2115/10; F21W 2131/202
  See application file for complete search history.

(56) References Cited

U.S. PATENT DOCUMENTS

| | | | | |
|---|---|---|---|---|
| 2007/0159818 | A1* | 7/2007 | Rueggeberg | A61C 13/082 362/231 |
| 2007/0259310 | A1* | 11/2007 | Goodson | A61C 1/088 433/29 |
| 2008/0060148 | A1* | 3/2008 | Pinyayev | A61B 5/0088 15/22.1 |
| 2008/0131836 | A1* | 6/2008 | Rueggeberg | A61C 13/082 433/29 |
| 2009/0091913 | A1* | 4/2009 | Li | F21V 13/04 362/33 |
| 2010/0053933 | A1 | 3/2010 | Meyer et al. | |
| 2010/0121198 | A1* | 5/2010 | West | A61B 1/00163 600/476 |
| 2010/0203465 | A1* | 8/2010 | Bria | F21S 48/1394 433/29 |
| 2010/0239998 | A1* | 9/2010 | Snyder | A61C 17/02 433/29 |
| 2011/0032350 | A1 | 2/2011 | Kikuchi et al. | |
| 2015/0064645 | A1* | 3/2015 | Jablow | A61C 19/066 433/29 |

FOREIGN PATENT DOCUMENTS

| | | |
|---|---|---|
| JP | 2005193012 A | 7/2005 |
| JP | 2005312727 A | 11/2005 |
| JP | 2006345908 A | 12/2006 |
| JP | 2009259703 A | 11/2009 |
| WO | 2009128391 A1 | 10/2009 |

OTHER PUBLICATIONS

Japanese Office Action from JP Application No. 2015-519312, dated Feb. 28, 2017.

* cited by examiner

PREOPERATIVE LIGHTING DEVICE

FIELD OF THE INVENTION

The present explanation relates to a dental lighting device, in particular a device comprising at least one supplementary light source connected to a supplementary instrument.

PRIOR ART

Conventionally, a predetermined dental zone to be operated on in a patient is lit by an operating light which provides ambient lighting which may prove insufficient for many dentistry procedures.

Such can be the case especially for a scaling procedure when the latter requires the use of coloured developers designed to penetrate the tartar to allow the tracking of tartar by fluorescence under particular lighting. Especially, it is common to use developers which emit by fluorescence in yellow when the developing substance is exposed to lighting in blue.

In this case, lighting of the dental zone to be operated on by ambient light only supplied by the operating light does not produce blue lighting required to cause a sufficient level of fluorescence of the developer to enable the dentist to sight the tartar accurately.

This absence of precision often compels the dentist to perform overtreatment, by addressing the tooth enamel more than is necessary.

Also, the dentist needs to view the dental zone with lighting substantially in white to be able to accurately make out the anatomical structures and the surfaces of the teeth to be worked on since otherwise the risk of performing overtreatment would be substantial here also.

There is consequently a pressing need to develop a dental lighting device for reducing the risks of overtreatment during a dentistry procedure carried out by means of a fluorescent developing substance.

PRESENTATION OF THE INVENTION

A first aspect of the present explanation relates to a dental lighting device comprising at least one lighting system configured to light a predetermined dental zone with, over a first spectral range which is less than a reference wavelength between 405 nm and 475 nm, a first average irradiance value E1 and, over a second spectral range greater than this reference wavelength, a second average irradiance value E2, which lighting system is configured to function according to at least one first lighting mode, in which the ratio of the first average irradiance value E1 to the second average irradiance value E2 is less than 12.

In this document, "average irradiance value" should be understood as the conventional radiometric definition of this term, that is to say, in the present circumstances, the average light power received per unit of area, and this value is calculated by integrating over the entire spectral range under consideration (i.e. the first or second spectral range within the context of the invention).

Unless specified otherwise, the terms "irradiance value" and "average irradiance value" shall be used interchangeably throughout this document.

A lighting device according to this first aspect comprises a lighting system which is configured to light a predetermined dental zone in a first colour formed by emission of one or more smaller wavelength(s) (to light said zone with a higher first colour temperature). In fact, this lighting system is configured to emit a first plurality of light beams in a first spectral range which is less than a reference wavelength between 405 nm and 475 nm (nanometers).

Accordingly, the light beams of this first plurality are emitted by the lighting system with respective emission wavelengths which are each less than this reference wavelength. The light beams of this first plurality are shaped by the lighting system to light the predetermined dental zone in the first colour with a first irradiance value E1.

This first irradiance value E1 therefore corresponds to the first flux, which is transported by all the light beams of the first plurality (i.e. by all the light beams which, on the one hand, impact the predetermined dental zone and which, on the other hand, are each emitted with their own emission wavelength which is less than the reference wavelength), divided by the surface area S of this dental zone.

Given the value of the reference wavelength which can arbitrarily be selected at any point of the spectral interval [405 nm; 475 nm], said first colour could be for example blue, indigo, violet, ultraviolet, or other. Therefore, within the scope of the present explanation this first colour will be generically called "colour blue" or "in blue" for reasons of simplicity.

Also, the lighting system of a lighting device according to the abovementioned first aspect is configured to also light the predetermined zone with a second colour formed by emission of one or more larger wavelength(s) (to also light said zone with a lower second colour temperature). In fact, this lighting system is configured to emit a second plurality of light beams in a second spectral range which is greater than the reference wavelength which by way of reminder is between 405 nm and 475 nm.

Accordingly, the light beams of this second plurality are emitted by the lighting system with respective emission wavelengths which are each greater than this reference wavelength. The light beams of this second plurality are shaped by the lighting system to light the predetermined dental zone in the second colour with a second irradiance value E2.

This second irradiance value E2 therefore corresponds to the second flux, which is transported by all the light beams of the second plurality (i.e. by all the beams which on the one hand impact the predetermined dental zone and which on the other hand are each emitted with their own emission wavelength which is greater than the reference wavelength), divided by the surface area S of this dental zone.

Given the value of the reference wavelength, which can arbitrarily be selected at any point of the spectral interval [405 nm; 475 nm], said second colour can be, for example, light warm white, warmer white, or another more monochromatic colour. Therefore, within the scope of the present explanation this second colour will be generically called "colour warmer than blue" for reasons of simplicity.

Accordingly, a dental lighting device according to the abovementioned first aspect is capable of lighting "in blue" the predetermined dental zone, with a first irradiance value E1, which makes fluorescence of a developer which must absorb radiation in this blue to reemit light beams by fluorescence easier, in particular in yellow.

Therefore, this lighting "in blue" contributes to better showing tartar by means of an adapted developer. All the same, this lighting in blue is not sufficient on its own to properly reduce the risks of overtreatment during a dentistry procedure performed by means of a fluorescent substance. In fact, the practitioner needs to be able not only to detect the tartar zones in the teeth but also accurately assess the anatomical structures of the teeth to reduce the risks of overtreatment during the dentistry procedure. Yet, as indicated earlier, this precise assessment of these anatomical structures requires observation of the dental zone with a substantially white light.

For this to occur, a dental lighting device according to the abovementioned first aspect is also capable of lighting the predetermined dental zone in a "colour warmer than blue", with a second irradiance value E2, which produces a unit colour resulting from the combined lighting of this zone with cumulatively the abovementioned first colour "in blue" and the abovementioned second colour "warmer than blue", which is different to this first colour and different to this second colour.

It eventuates that the practitioner can observe the anatomical structures of the teeth under this unit colour which is different to the first colour "in blue". All the same, producing such a unit colour is not sufficient per se to properly reduce the risks of overtreatment during the dentistry procedure. In fact, this unit colour must not be oversaturated in first colour "in blue" to enable the dentist to accurately assess the anatomical structures of the teeth.

In this perspective, a dental lighting device according to the abovementioned first aspect is configured especially so that this unit colour is obtained with particular proportions of first and second colours which allow this unit colour to not be oversaturated in first colour "in blue".

It proves that the human eye is less sensitive in blue than in other warmer colours (or bigger wavelength than this blue), such that it is possible to provide a first irradiance value E1 larger than the second irradiance value E2 (and therefore a value greater than 1 for said ratio E1/E2), without this colour surplus "in blue" having any significant impact on the unit colour such as perceived by the practitioner, on condition however that such colour surplus "in blue" is not excessive.

The research and development work conducted by the inventors and specified at the outset of the present explanation has shown that preferred observation conditions were obtained when the ratio E1/E2, corresponding to division of the first irradiance value E1 "in blue" by the second irradiance value E2 in a colour "warmer than blue", does not exceed a threshold of around 12 (around twelve). Therefore, the lighting system of a dental lighting device according to the above mentioned first aspect is configured to function according to at least one first lighting mode (i.e. by choice, according to only this first mode or according to also at least one second mode distinct from said first mode), in which the ratio of the first irradiance value E1 to the second irradiance value E2 is less than 12.

Accordingly, at the outset of the present explanation the inventors have definitively developed a dental lighting device according to the abovementioned first aspect, which reduces the risks of overtreatment during a dentistry procedure performed by means of a fluorescent developing substance.

In fact, according to this first aspect the device is capable of lighting a predetermined dental zone "in blue" to allow the practitioner to detect those places in the mouth of the patient which are to be treated by fluorescence, and, cumulatively, in a colour "warmer than blue", to rebalance the unit colour which is perceived by the practitioner as approaching a colour less saturated in blue colour so he can assess more accurately the anatomical structures of the teeth relative to said abovementioned places, such rebalancing being adequately obtained when the proportion of lighting "in blue" relative to the proportion of lighting in a colour "warmer than blue" does not exceed a threshold value of around 12.

Also, this threshold value can be optimised in some cases, especially to consider the levels of contrasts between portions of scaled enamel and portions of enamel devoid of tartar, which are perceived by some practitioners for some types of teeth.

Accordingly, in some embodiments, the ratio, in the first lighting mode, of the first irradiance value E1 to the second irradiance value E2 can be provided less than, by choice, at least any one of the values hereinbelow: 14; 12; 10; 8; 6; 4; 2.

Also, this threshold value could be optimised in the future, especially to take into account any other constraints reported by clients and/or results of any additional developmental work. Supplementary clinical trials conducted by the applicant thus made it possible to verify that optimal performances are indeed obtained when the ratio E1/E2 is less than 12. Compliance with this particular upper threshold (i.e. 12) provides preferential observation conditions and enables in particular the practitioner to appreciate accurately the anatomical structures and reliefs of the teeth to be treated.

In some embodiments, the ratio in the first lighting mode of the first irradiance value E1 to the second irradiance value E2 can be provided as greater by choice than at least any one of the values hereinbelow: 1; 2; 4; 6; 8. The fact also of providing a lower threshold for the ratio E1/E2 can permit optimisation of the first irradiance value E1 and especially favour fluorescence of the place to be worked on by means of a developer. These examples of low threshold values take into account the above remark, specifically that the human eye is less sensitive in blue than in the other primary colours. They also consider the fact that a portion of scaled enamel exhibits reflectivity less than that of a portion of enamel devoid of tartar, less rough.

In some embodiments, the irradiance system can be configured in the first lighting mode to light the predetermined dental zone with the first irradiance value E1 which is provided greater than 1 $W/m^2$. Such a minimal value for the first irradiance value E1 can correspond especially to a threshold value below which it becomes less easy to perceive the fluorescence of places to be worked on.

In some embodiments, the lighting system can be configured, in the first lighting mode, to light the predetermined dental zone with the first irradiance value E1 which is provided greater than, by choice, at least any one of the values hereinbelow: 5 $W/m^2$; 10 $W/m^2$; 15 $W/m^2$; 20 $W/m^2$; 30 $W/m^2$; 40 $W/m^2$; 50 $W/m^2$. Above this value of 50 $W/m^2$, the output of fluorescence emission of the developing substance can drop drastically, whereas the flux reflected by the enamel, especially in specular terms, can reach a power level which dazzles the practitioner.

In some embodiments, the lighting system can be configured, in the first lighting mode, to light the predetermined dental zone with the first irradiance value E1 which is provided less than 300 $W/m^2$, or even less than 100 $W/m^2$, for example, which can especially take into account the issues mentioned above, and make it easier to reduce the dimensions of the lighting system.

In some embodiments, the dental lighting device can comprise a control system coupled to the lighting system and configured to control the operation of said lighting system according to at least the first lighting mode. This control system can form an integral part of the lighting system, or can be separate from the latter.

In some embodiments, the dental lighting device can be such that the reference wavelength is between a minimal MIN value which is greater than 405 nm, and a maximal MAX value which is less than 475 nm. In fact, in some applications the tolerance interval defined by these MIN and MAX values can be provided smaller than the interval [405 nm; 475 nm]. This [MIN; MAX] tolerance interval can be provided centred on a preferred fluorescence wavelength of a particular developer to be used.

In this way for example, the minimal MIN value can be selected, by choice, to be equal to any one of the values hereinbelow: 410 nm; 420 nm; 430 nm; 440 nm; 450 nm; 460 nm; 470 nm. Similarly, the maximal MAX value can be selected, by choice, to be equal to any one of the values hereinbelow: 470 nm; 460 nm; 450 nm; 440 nm; 430 nm; 420 nm; 410 nm.

It is specified that any of these examples of MIN values can be selected in combination with any of these examples of MAX values to define the abovementioned tolerance interval, provided only that the selected MIN value is less than or equal to the selected MAX value. For example, by way of illustration and non-limiting, the dental lighting device can be such that the reference wavelength is between 440 nm and 460 nm.

In some embodiments, the dental lighting device can be such that the width of the abovementioned tolerance interval [MIN; MAX] (which width corresponds to the difference between the MAX value and the MIN value) is less than 20 nm. By way of non-limiting example, such a width value can correspond to the width of a particular emission peak of a relevant light-emitting diode, when it is selected to equip the lighting system with at least one such diode.

In some embodiments, the dental lighting device can be such that the first spectral range is between 370 nm and the reference wavelength. Accordingly, the first spectral range can be entirely contained in the visible spectrum.

In some embodiments, the dental lighting device can be such that the second spectral range is between the reference wavelength and 780 nm. Accordingly, the second spectral range can be entirely contained in the visible spectrum.

In some embodiments, the dental lighting device can comprise an operating light and the lighting system can comprise at least one ambient light source connected to this operating light. Accordingly, the first irradiance value E1 and the second irradiance value E2 can each be at least partly obtained by means of such an ambient light source.

In some embodiments, the dental lighting device can comprise a supplementary instrument, and the lighting system can comprise at least one supplementary light source connected to this supplementary instrument. Accordingly, the first irradiance value E1 and the second irradiance value E2 can each be at least partly obtained by means of this at least one supplementary light source.

In some embodiments, the dental lighting device can be such that the first irradiance value E1 and the second irradiance value E2 are each obtained integrally by means of only this at least one supplementary light source. In other terms, it is not necessary to use supplementary lighting, in particular the ambient light source of an operating light, to obtain the preferred values E1 and E2.

In some embodiments, the dental lighting device can cumulatively comprise the abovementioned operating light and the abovementioned instrument. Accordingly, the first irradiance value E1 and the second irradiance value E2 can each be obtained by way of the cumulative lighting supplied respectively by said at least one supplementary light source connected to this instrument and by the ambient light source connected to this operating light.

In some embodiments, the supplementary instrument can comprise at least one portion having dimensions adapted to enable introduction of this portion into the mouth of a patient, which can allow said at least one supplementary light source to be near the predetermined dental zone when it lights the latter.

In some embodiments, the supplementary instrument can comprise a body having a fixing part capable of cooperating with a tool to fix said tool and the body relative to each other, and at least one housing arranged in the region of the fixing part and in which is mounted said at least one supplementary light source. Such a body can for example make prehension of the instrument easier. Therefore, the supplementary instrument can serve as work tool for the practitioner for performing a particular dentistry procedure, and ensure preferred lighting to allow this practitioner to best assess the anatomical structures and the places to be worked on. Accordingly, combining these two functions into one and the same instrument helps reduce the number of items to be handled at the same time during the dentistry procedure and, obviously, make this procedure easier.

In some embodiments, said tool can be a scaling tool (a scaler), which can make a scaling procedure more precise and/or easier, whereby the tool can be placed near the dental zone lit by the at least one supplementary light source.

In some embodiments, said instrument can comprise prehension means, for example a sleeve which is attached to the abovementioned body, when the instrument comprises such a body, and which is capable of be gripped by the whole hand to make it easier to move said instrument.

In some embodiments, the lighting system can comprise a plurality of supplementary discrete light sources. In other words, such a lighting system can comprise, by choice, two or more supplementary light sources which are each separate from each other, for example spaced apart from each other. Such a configuration can make producing the preferred lighting conditions easier.

In some embodiments, the lighting system can comprise at least two supplementary light sources having separate emission spectra. Such a configuration can make producing the preferred lighting conditions easier. For example, the lighting system can be such that a first of these two supplementary light sources contributes more to producing the first irradiance value E1 than the other of these two sources, and such that said other of these two sources contributes more to producing the second irradiance value E2 than said first of these two sources.

In some embodiments, the lighting system can comprise a luminous flux mixer, for example a light guide, at the input of which luminous fluxes emitted respectively by the supplementary light sources are injected, and at the output of which a light beam emerges which is adapted to contribute in all or part to lighting the predetermined dental zone with the first irradiance value E1 and the second irradiance value E2. Such a luminous flux mixer can make it easier to combine into a single light beam several luminous fluxes which are emitted respectively by the different supplementary light sources of the lighting system.

In some embodiments, the lighting system can be configured to emit a light beam, for example a beam which emerges from the abovementioned luminous flux mixer, which has, over the first spectral range, a first intensity value I1 and, on the second spectral range, a second intensity value I2, and the lighting system can be configured so that when it operates according to the first lighting mode the ratio of the first intensity value I1 to the second intensity value I2 is less than 13 (thirteen).

This maximal value of the ratio I1/I2, determined at the level of an output of the lighting system, is to be matched to the abovementioned maximal value of the ratio E1/E2, determined at the level of the predetermined dental zone, after propagation of light beams, in particular from said output of the lighting system. It is deliberately chosen for a greater maximal value for the ratio I1/I2 than for the ratio E1/E2 to consider the influence on the irradiance values in the predetermined dental zone which any other light beams might have and which would be obtained by means other than the supplementary light sources of the device and would be likely to impact said zone.

In some embodiments, the or each supplementary light source can comprise a light-emitting diode, which can allow the device to be implemented inexpensively.

In some embodiments, when it comprises at least two light-emitting diodes the lighting system can be such that each of these two diodes has an emission spectrum separate from each other.

In some embodiments, the lighting system can be also configured to function according to at least one second lighting mode distinct from the first, the device then comprising a switch configured to switch functioning of the lighting system between the first lighting mode and the second lighting mode. Accordingly, the dental lighting device can have greater modularity of use, as the switch is configured to switch operation of the lighting system from the first lighting mode to its second lighting mode, and vice versa.

In some embodiments, the lighting system can be configured so that the ratio of the first irradiance value E1 to the second irradiance value E2 has different values in the first lighting mode and in the second lighting mode, respectively. In other words, this ratio E1/E2 can have a first value R1, in the first lighting mode, and a second value R2, in the second lighting mode, with R1 different to R2.

In some embodiments, the lighting system can be configured so that the ratio of the first irradiance value E1 to the second irradiance value E2 is greater in the first lighting mode than in the second lighting mode, which means that the abovementioned first value R1 is greater than the abovementioned second value R2.

Such a decrease in the ratio E1/E2, in moving from the first lighting mode to the second lighting mode, can especially consider the evolution of contrast between a portion of bared enamel (i.e. devoid of tartar) and a portion of scaled enamel as a function of the age of the tooth.

In fact, it is usually noted that the enamel has porosity which is accentuated with age. Accordingly, when the tooth is young (i.e. usually when the tooth is older than around 25 years), the enamel is slightly porous. Therefore, a developing substance can easily penetrate inside food residue fixed to a portion of scaled enamel, but finds it difficult to penetrate inside a portion of enamel devoid of tartar. It eventuates that said portion of scaled enamel fluoresces much more than said portion of enamel devoid of tartar such that these two portions can be perceived with pronounced contrast. However, when the tooth ages this contrast decreases since the enamel becomes more porous. In fact, the developing substance can more easily penetrate the enamel of the portion devoid of tartar. It eventuates that this portion devoid of tartar fluoresces more, which makes it hard to perceive relative to the portion of scaled enamel, which it continues to fluoresce substantially.

Accordingly, the abovementioned second lighting mode can be used to boost the second irradiance value E2 relative to the first irradiance value E1, such that the dental zone is lit with more wavelengths to which the developing substance is not sensitive (i.e. wavelengths which are not likely to excite fluorescence emission of this substance). An increase of the luminous flux reflected specularly on the tooth can eventuate and obviously the planned increase in contrast. In fact, the reflectivity of a portion of bared enamel is bigger than the reflectivity of a scaled portion.

In some embodiments, the lighting system can be configured so that the ratio of the first irradiance value E1 to the second irradiance value E2 is smaller in the first lighting mode than in the second lighting mode, which means that the abovementioned first value R1 is less than the abovementioned second value R2.

Such a rise in the ratio E1/E2 when moving from the first lighting mode to the second lighting mode can especially improve the visibility of fluorescence generated by the lighting of the dental zone with the first colour "in blue". Accordingly, in moving from the first lighting mode to the second lighting mode and vice versa, the practitioner can adjust his perception as needed and take into account the specificities of the teeth of the patient.

In some embodiments, the lighting system can be configured so that the ratio R2/R1, between the second value R2 of the ratio E1/E2 in the second lighting mode and the first value R1 of said ratio in the first lighting mode, is by choice between any two values of all the values hereinbelow: 2; 5; 10; 20. More generally, supplementary clinical trials conducted by the applicant made it possible to verify that optimal performances of the device of the invention are obtained when the ratio R1/R2 is between 2 and 20 (higher and lower limits included), or between 0.05 and 0.5 (higher and lower limits included), depending on the mode that is qualified as a "first" lighting mode or a "second" lighting mode. The value of this ratio R2/R1 could be determined as a function of the needs of the practitioner in terms of perception of the portions of bared enamel relative to the portions of scaled enamels.

In some embodiments, the switch can be configured to switch operation of the lighting system between the first lighting mode and the second lighting mode by varying one of the two values of the first irradiance value E1 and the second irradiance value E2, whereas the other of these two values remains unchanged. This configuration represents a solution simple for executing the abovementioned switching operation. It can also better show the portions of scaled enamels relative to the portions of bared enamel by varying only anyone flux of the fluxes reflected specularly onto the teeth and the fluxes emitted by fluorescence of the developer which a penetrated the teeth.

In some embodiments, the switch can be configured to switch operation of the lighting system between the first lighting mode and the second lighting mode by varying only the second irradiance value E2, whereas the first irradiance value E1 remains unchanged.

In some embodiments, the switch can be configured to switch operation of the lighting system between the first lighting mode and the second lighting mode by varying only the first irradiance value E1, whereas the second irradiance value E2 remains unchanged.

In some embodiments, the switch can comprise an actuator, for example an interrupter, a variator or other, capable of be handled by the user to switch operation of the lighting system between the first lighting mode and the second lighting mode, which can allow the practitioner to select the most opportune instant to make this switch.

In some embodiments, the switch can be configured to automatically (i.e. without action on the part of the user) and repetitively (for example, periodically, at a predetermined frequency) switch operation of the lighting system between the first lighting mode and the second lighting mode.

Accordingly, this periodic switching between the two lighting modes can let the practitioner more accurately observe the portions of scaled teeth and the portions of teeth devoid of tartar by repetitive variation of the contrast between these different portions caused by this periodic switching without the practitioner needing to interfere with the device.

A second aspect of the present explanation relates to a lighting configuration process using a dental lighting device according to the first aspect detailed hereinabove in the present explanation.

This process comprises a configuration step of the lighting system, during which the lighting system is configured to that it operates according to at least one first lighting mode in which said lighting system lights a predetermined dental zone, over a first spectral range which is less than a reference wavelength between 405 nm and 475 nm, with a first irradiance value E1 and a second irradiance value E2, over a second spectral range greater than this reference wavelength, and in which the ratio of the first irradiance value E1 to the second irradiance value E2 is less than 12.

The abovementioned characteristics and advantages and others will emerge more clearly from the following detailed description of embodiments which are devoid of any limiting character and which are proposed simply by way of illustration. This detailed description refers to the attached drawings.

BRIEF DESCRIPTION OF THE DRAWINGS

The attached drawings are schematic and are not to scale; their chief aim is to illustrate the principles mentioned in the present explanation. In these attached drawings.

DETAILED DESCRIPTION OF EMBODIMENTS

First Embodiment

Figure 6A:
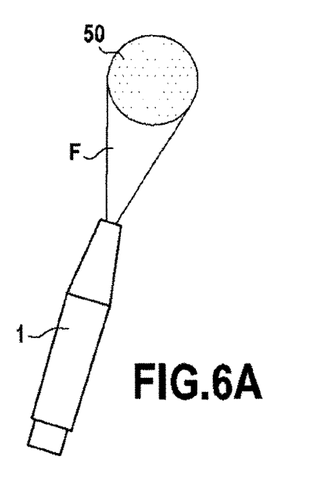
FIG. 6A schematically shows the lighting of a predetermined dental zone by the device according to the abovementioned first or second embodiment.

As illustrated in FIG. 6A, a dental lighting device according to this first example comprises a lighting system configured to light a predetermined dental zone 50.

Within the scope of the present explanation, the expression "a predetermined dental zone" designates a surface located in an imaginary plane whereof the characteristic dimensions are of the order of magnitude of those of the anatomical part which is usually observed by a practitioner during a dentistry procedure.

For example, this surface can exhibit characteristic dimensions between 0.5 centimeters and 5 centimeters, for example between 1 centimeter and 3 centimeters.

FIG. 6A arbitrarily and non-limiting illustrates this surface by way of a disc the diameter of which is equal to a characteristic dimension of the type of those previously described. Without departing from the scope of the present explanation, any other form could be provided for this surface (for example a rectangle or a square whereof the sides are equal to the dimensions characteristic of the type of those previously described), provided only that its characteristic dimensions were of the abovementioned order of magnitude.

Figures 1A, 1B, 1C:
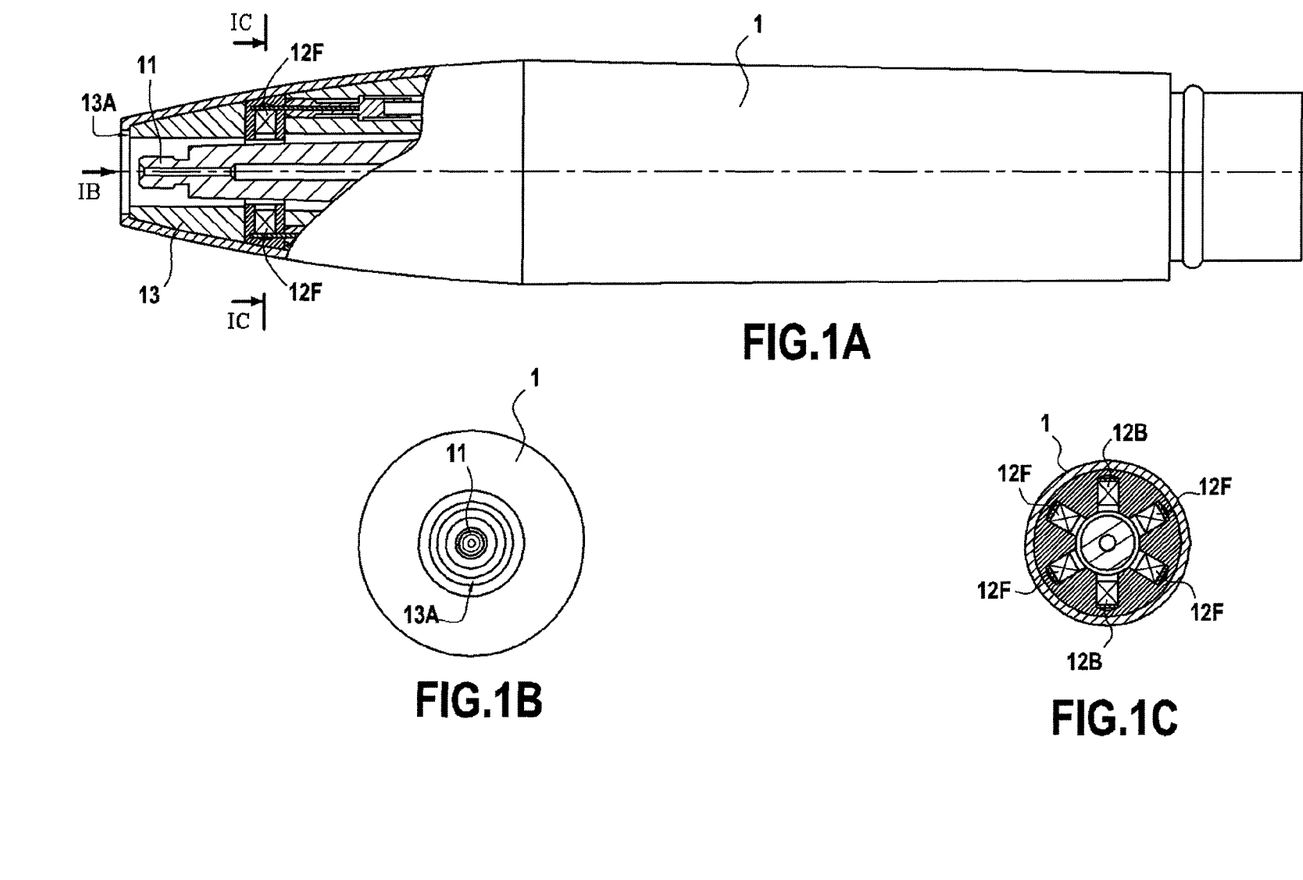
FIGS. 1A, 1B and 1C show respectively a partial sectional view, a frontal view and a sectional view IC-IC of a first embodiment of a dental lighting device according to the present explanation.

According to this example, the dental lighting device comprises a supplementary instrument 1, seen better in FIGS. 1A to 1C, and the lighting system comprises at least one supplementary light source connected to this instrument 1.

According to this example, the lighting system of this instrument 1 is configured to emit a first luminous flux F which, after propagation, lights the dental zone 50.

Figure 7:
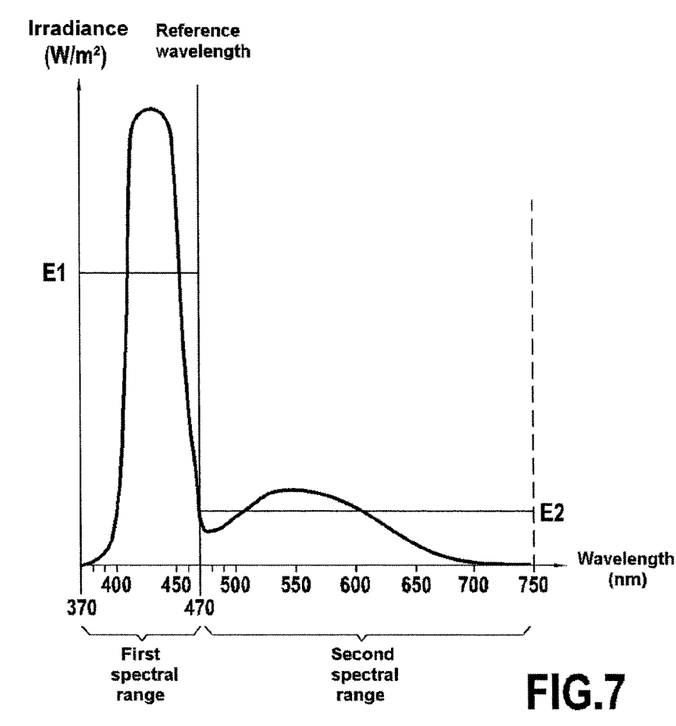
FIG. 7 is a graphic schematically illustrating an example of determination of the first irradiance value E1 and of the second irradiance value E2 according to any one of the abovementioned three embodiments.

In particular, as illustrated in FIG. 7, the lighting system of this instrument 1 is configured to light the dental zone 50, over a first spectral range which is less than a reference wavelength between 405 nm and 475 nm, with a first irradiance value E1 and, over a second spectral range greater than this reference wavelength, a second irradiance value E2.

As already indicated above, in this document, "irradiance value" or more precisely "average irradiance value" should be understood as the conventional radiometric definition of this term, that is to say, in the present circumstances, the average light power received per unit of area, and this value is calculated by integrating over the entire spectral range under consideration (i.e. the first or second spectral range within the context of the invention).

More particularly, according to this example the reference wavelength is selected equal to 470 nm; the first spectral range is between a lower limit, equal to 370 nm, and this reference wavelength at 470 nm; and the second spectral range is between this reference wavelength at 470 nm and an upper limit, equal to 750 nm.

Also, according to this example the lighting system is configured to emit a first plurality of light beams, with a first continuous spectrum, which is also over the entire extent of the first spectral range. Accordingly, each light beam belonging to this first plurality is emitted by the lighting system at a wavelength included in the first spectral range, in particular between 370 nm and 470 nm.

Without departing from the scope of the present explanation, it could be provided however that the lighting system is configured to emit this first plurality of light beams with a discontinuous spectrum and/or one not spreading over the entire extent of the first spectral range (emitting for example one or more bands or stripes spaced apart from each other, each of these bands or stripes having a central wavelength included in the first spectral range).

Also, after propagation, the light beams of the first plurality emitted in this way light up the dental zone 50 with a first irradiance value E1.

According to this example, this first irradiance value E1 is calculated as follows:

for each wavelength L1 belonging to the first spectral range, the elementary irradiance dE1(L1) as is calculated follows:
for each point of coordinates (x, y) belonging to the surface S defining the dental zone 50, the elementary irradiance $d^2E1(x, y, L1)$ is calculated;
the average value of this elementary irradiance $d^2E1(x, y, L1)$ over the entire surface S is calculated to determine dE1(L1);
the average value of this elementary irradiance dE1 (L1) over the entire first spectral range is calculated to determine the value E1.

The first average irradiance value E1 is thereby obtained. This value E1 is equivalent to the average light power received per unit of area and is calculated by integrating over the entire first spectral range.

In addition, according to this example, the lighting system is configured to emit a second plurality of light beams, with a second continuous spectrum, which is also over the entire extent of the second spectral range. Accordingly, each light beam which belongs to this second plurality is emitted by the lighting system at a wavelength which is included in the second spectral range, in particular between 470 nm and 750 nm.

Without departing from the scope of the present explanation, it could however be provided that the lighting system is configured to emit this second plurality of light beams with a discontinuous spectrum and/or one not spreading over the entire extent of the second spectral range (emitting for example one or more bands or stripes spaced apart from each other, each of these bands or stripes having a central wavelength included in the second spectral range).

Also, after propagation, the light beams of the second plurality emitted in this way together light up the dental zone 50 with a second irradiance value E2.

According to this example, this second irradiance value E2 is calculated as follows:

for each wavelength L2 belonging to the second spectral range the elementary irradiance dE2(L2) is calculated as follows:
for each point of coordinates (x, y) belonging to the surface S defining the dental zone 50, the elementary irradiance $d^2E2(x, y, L2)$ is calculated;
the average value of this elementary irradiance $d^2E2(x, y, L2)$ over the entire surface S is calculated to determine dE2(L2);
the average value of this elementary irradiance dE2(L2) over the entire second spectral range is calculated to determine the value E2.

The second average irradiance value E2 is thereby obtained. This value E2 is equivalent to the average light power received per unit of area and is calculated by integrating over the entire second spectral range.

According to this example, the lighting system is configured to function only according to a first and single lighting mode in which the ratio of the first irradiance value E1 to the second irradiance value E2 is less than a predetermined threshold value.

In this example, this ratio E1/E2 in this first lighting mode is selected equal to around 8 (eight).

The supplementary instrument 1 which comprises this lighting system will now be described in greater detail by means of FIGS. 1A to 1C.

According to this example, this supplementary instrument comprises a body having a fixing part 11 capable of cooperating with a tool (not shown, this tool can for example be a conventional scaling tool) to fix said tool and the body relative to each other.

According to this example, the fixing part 11 corresponds to an end part of the body 1, and has dimensions adapted to allow this end part to be introduced into the mouth of a patient to perform a dentistry procedure by way of the tool to be fixed on said body 1.

Also, the lighting system comprises a plurality of supplementary light sources, separate from each other.

Figure 2:
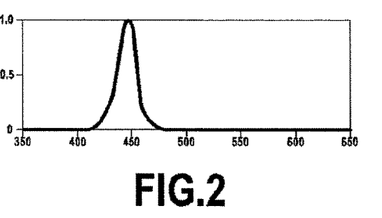
FIG. 2 shows the emission spectrum of a light-emitting diode of a first category used in this first example.
Figure 3A:
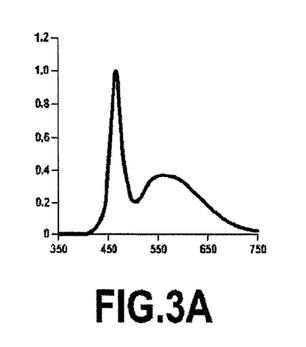
FIGS. 3A and 3B show different choices of emission spectra for a light-emitting diode of second category used in this first example.
Figure 3B:
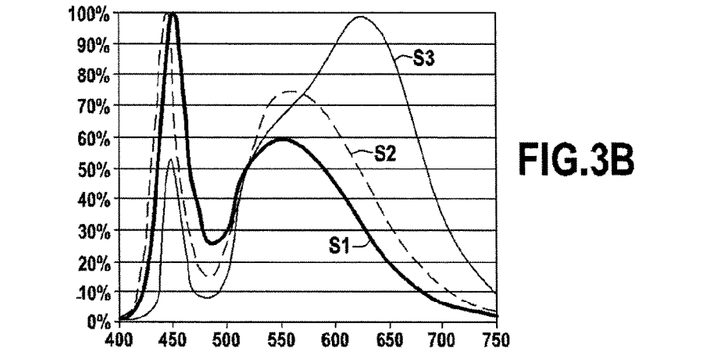

According to this example, the lighting system comprises a first group comprising one or more supplementary light sources, each of which has one and the same identical first emission spectrum (better seen in FIG. 2); and at least one second group comprising one or more other supplementary light sources, each of which has one and the same second emission spectrum, different to the first emission spectrum (clearer in FIGS. 3A and 3B, which have different variants of this second spectrum).

In particular, in this example the abovementioned first group comprises four supplementary light sources, whereas the abovementioned second group comprises two supplementary light sources. Accordingly, in this example the lighting system comprises a total of six supplementary light sources.

More particularly, each of these six supplementary light sources comprises a light-emitting diode. Accordingly, in this example, the abovementioned first group comprises four light-emitting diodes 12F, each of which presents the abovementioned first emission spectrum. Put otherwise, the abovementioned second group comprises two light-emitting diodes 12B, each of which presents the abovementioned second emission spectrum.

Also, according to this example, the supplementary instrument has a plurality of housings, in which the plurality of supplementary light sources 12F, 12B is respectively mounted. In this example, these housings are arranged angularly at substantially regular intervals (see FIG. 1C), in the region of the fixing part 11, in particular slightly back from the end from which the tool is intended to project from the body 1.

In addition, according to this example the lighting system comprises a luminous flux mixer, in particular a light guide 13, at the input of which luminous fluxes respectively emitted by each of the diodes 12F, 12B are injected, and at the output 13A of which a light beam F emerges (better seen in FIG. 6A) adapted, as such, to enable lighting of the dental zone 50 with the planned first and second irradiance values E1 and E2.

In particular, this light guide 13, seen front on in FIG. 1B, is shaped, at least at output, into a light crown 13A. It guides light from the diodes 12F, 12B to the end of the body 1 from which the tool is designed to project.

Also, FIG. 2 illustrates the first emission spectrum of each of the diodes 12F of the abovementioned first group.

According to this example, this first spectrum comprises a single width peak at mid-height around 20 nm and centred on a wavelength around 450 nm. Accordingly, each diode 12F of the first group emits light beams only in the first spectral range defined in FIG. 7.

Therefore, each diode 12F participates only in forming at least part of the lighting "in blue" of the dental zone 50 for the purpose of producing the first irradiance value E1. Inversely, these diodes 12F make no contribution to producing lighting in a colour "warmer than blue" of this zone 50 with the second irradiance value E2.

Also, FIG. 3A illustrates a first variant S1 of the second emission spectrum of each of the diodes 12B of the abovementioned second group.

In particular, this second spectrum according to this first variant comprises a first peak of greater intensity, and a second peak of lesser intensity.

More particularly, this first peak is centred on a first wavelength smaller than a second wavelength on which the abovementioned second peak is centred. Especially, these first and second wavelengths are respectively equal to around 455 nm and around 560 nm.

In addition, this first peak has a width at mid-height smaller than that of the second peak (especially around 20 nm as opposed to around 120 nm).

Therefore, each diode 12B participates actively not only in forming at least part of the lighting "in blue" of the dental zone 50 for the purpose of producing the first irradiance value E1, but also participates actively in forming at least part of the lighting in a colour "warmer than blue" of this zone 50 for the purpose of producing the second irradiance value E2.

Also, the colour temperature associated with this second emission spectrum according to this first variant S1 is around 6500 K.

In addition, in addition to the abovementioned first variant S1, FIG. 3B illustrates second and third variants S2 and S3 of the second emission spectrum of the diodes 12B of the second group.

These second and third variants S2 and S3 are similar to the first variant S1, such that their description will not be repeated in detail. They do have however the few differences mentioned hereinbelow.

The second variant S2, and even more the third variant S3, contribute more to producing the second irradiance value E2, their second respective peaks being more pronounced than the second peak of the first variant S1.

Also, the third variant S3 participates substantially less in producing the first irradiance value E1, its first peak being lessened relative to the first respective peaks of the first variant S1 and of the second variant S2, substantially equal.

Finally, the colour temperature associated with the second variant S2 is around 4500K, whereas that associated with the third variant S3 is around 3000 K.

Also, according to this example the dental lighting device comprises a control system (not shown) coupled to the lighting system and configured to control operation of said lighting system according to the abovementioned first lighting mode.

In particular, the control system is configured to generate a plurality of control signals which are respectively transmitted to the plurality of diodes 12B, 12F of the lighting system to control their light emission.

Especially, in this single first lighting mode these control signals adopt respective first signal values which are adapted to let the lighting system light up the dental zone 50 with the ratio E1/E2 equal, in this example, around 8 as previously indicated.

Second Embodiment

By way of FIGS. 4 to 5D, a dental lighting device according to a second embodiment according to the present explanation will now be described.

A dental lighting device according to this second embodiment differs from the dental lighting device according to the first embodiment previously described, only in that the lighting system of the dental lighting device according to this second example is configured to function according to not only the first lighting mode described in association with the first example, but also according to at least one second lighting mode distinct from this first mode. In fact, as indicated during the description of the first embodiment, the lighting system of the dental lighting device according to this first example is configured to function according to the first lighting mode only.

In particular, according to this second example, the lighting system is configured to function according to any mode of:
- the first lighting mode previously described in association with the first example. This first lighting mode produces a first value R1 for the ratio E1/E2;
- a second lighting mode, distinct from this first mode, which produces a second value R2 pour the ratio E1/E2 which is less than R1;
- and a third lighting mode, distinct from this first mode and this second mode, which produces a third value R3 for the ratio E1/E2 which is less than R2;

It should be noted that alternative to this second example, the lighting system could be configured to switch only between the first and second lighting modes as mentioned above.

According to this second example, moving from one lighting mode to another is done by means of a switch (not shown) which is configured to switch operation of the lighting system from one mode to another.

In particular, the switch of a device according to this second example is coupled to the control system (which is described in more detail in association with the abovementioned first embodiment), and is configured to switch the control system from one lighting mode to another.

Also, the switch is configured to cause variations in the respective values of all or some of the control signals generated by the control system, so as to vary the ratio E1/E2 between the abovementioned three values R1, R2 and R3 from one lighting mode to another.

Figures 4, 5A, 5B, 5C, 5D:
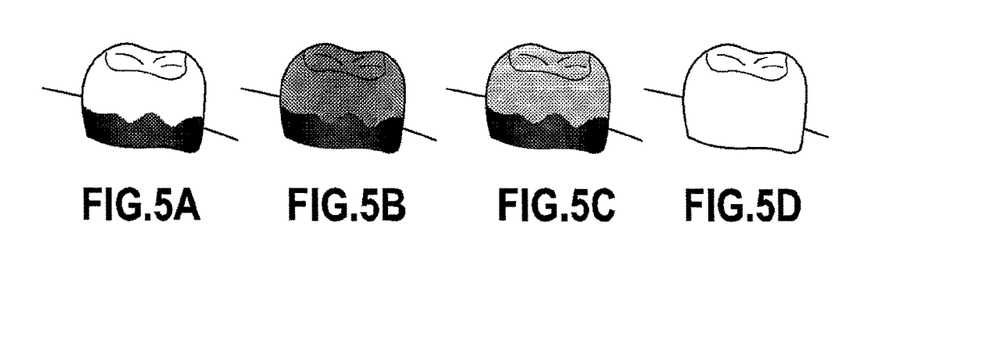
FIG. 4 schematically shows the evolution of the ratios of values of the control signals of the abovementioned diodes as a function of the selected lighting mode with a second embodiment of a dental lighting device according to the present explanation.
FIGS. 5A, 5B, 5C and 5D show contrast evolutions between portions of bared enamel and portions of scaled enamel, obtained with the device according to the abovementioned second example, as a function of the selected lighting mode.

In particular, as illustrated in FIG. 4, in the first lighting mode the control signals respectively associated with the diodes 12B of the second group of diodes each adopt a value N1, whereas the control signals respectively associated with the diodes 12F of the first group of diodes each adopt a value N4.

In addition, in the second lighting mode the control signals respectively associated with the diodes 12B of the second group of diodes each adopt a value N2 greater than N1, whereas the control signals respectively associated with the diodes 12F of the first group of diodes each adopt the abovementioned value N4.

Finally, in the third lighting mode the control signals respectively associated with the diodes 12B of the second group of diodes each adopt a value N3 greater than N2, whereas the control signals respectively associated with the diodes 12F of the first group of diodes each adopt the abovementioned value N4.

Therefore, the fact that the value N3 is greater than the value N2, which in turn is greater than N1, whereas the value N4 remains unchanged for the three lighting modes, means that the first value R1 is greater than the second value R2 which in turn is greater than the third value R3.

Also, in this example, the control signals respectively associated with the diodes 12F of the first group of diodes can be binary signals (all or nothing), since it is not necessary for them to generate other non-zero values than the abovementioned value N4.

From another perspective, in this example the control signals respectively associated with the diodes 12B of the second group of diodes can be analog or digital signals adapted to sequentially generate at least the abovementioned three non-zero values N1, N2 and N3.

By way of illustrative and non-limiting example, R1 is selected arbitrarily equal to 8, R2 equal to 5 and R3 equal to 1.5. This shows the contrasts illustrated in FIGS. 5A to 5D described hereinbelow. As indicated above, optimal observation conditions are obtained when the ratio between the ratios E1/E2 for each switching operation of lighting mode is between 2 and 20 (limits included) or, where appropriate, between 0.05 and 0.5 (limits included).

In particular, FIG. 5A shows the perception which a practitioner can have of a first tooth, whereof the enamel is slightly porous, when this tooth is lit under the first lighting mode, with the first value R1. In this case, the contrast between scaled portions of the tooth and portions of the tooth devoid of tartar is good since the developing substance does not easily penetrate these portions devoid of tartar, such that the flux reflected specularly by these portions devoid of tartar is preponderant over the fluxes that they emit no fluorescence from the developing substance, and even if the tooth is lit with a second irradiance value E2 which is weak relative to the first irradiance value E1. Therefore, the first lighting mode can be qualified as a mode adapted for observation of the tartar for slightly porous enamel.

Also, FIG. 5B shows the perception which a practitioner can have of a second tooth, whereof the enamel is more porous than that of the abovementioned first tooth when this second tooth is lit also under the first lighting mode with the first value R1. In this case, the contrast between scaled portions of the tooth and portions of the tooth devoid of tartar is mediocre since the developing substance can easily penetrate these portions devoid of tartar. It eventuates that the second irradiance value E2 this time is insufficient relative to the first irradiance value E1 to let the flux reflected specularly by the surface of the enamel of these portions devoid of tartar be substantially greater than the flux emitted by fluorescence from the porous interior of these portions. The practitioner then perceives a yellowish colour for the whole of the tooth.

To rectify this problem, this second tooth can be observed under the second lighting mode, in which the flux reflected specularly is augmented relative to the flux emitted by fluorescence, due to the fact that the second value R2 of the ratio E1/E2 is less than the first value R1, without as such masking the lighting "in blue" which results from the first irradiance value E1. Therefore, the practitioner can observe this second tooth with the contrast illustrated in FIG. 5C. The second lighting mode can be qualified as a mode adapted for observation of tartar for substantially porous enamel.

Finally, FIG. 5D shows the perception which a practitioner can have of the first tooth or of the abovementioned second tooth, when they are lit under the third lighting mode. In this third mode, the flux reflected specularly is still more augmented relative to the flux emitted by fluorescence, due to the fact that the third value R3 of the ratio E1/E2 is less than the second value R2. But this time the second irradiance value E2 is too much relative to the first irradiance value E1 such that the lighting in the colour "warmer than blue" substantially masks the lighting "in blue". It eventuates that in this third lighting mode contrast is poor, and only the anatomical structure of the tooth can be observed by the practitioner due to the specular reflections from the surface of the enamel which he sees. The third lighting mode can be qualified as a mode adapted for observation of the tooth without revealing the tartar.

It is pointed out that all other characteristics described in association with the first embodiment, which have not been described again in association with the second embodiment for streamlining the size of the present explanation, can evidently be repeated, by choice, alone or in combination, by this second embodiment.

Third Embodiment

Figure 6B:
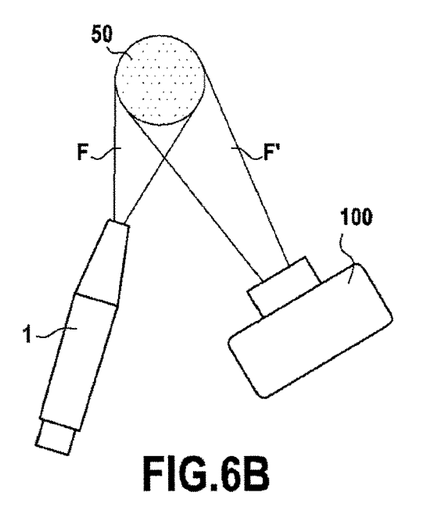
FIG. 6B schematically shows the lighting of a predetermined dental zone by a dental lighting device according to a third embodiment according to the present explanation.

FIG. 6B illustrates a dental lighting device according to a third embodiment according to the present explanation.

A dental lighting device according to this third embodiment differs from the dental lighting devices according to the first and second embodiments previously described, only in that the lighting system of the dental lighting device according to the third example comprises not only a supplementary instrument 1, which integrates a plurality of supplementary light sources configured to light the surface of the dental zone 50 with a first luminous flux F, but also an operating light 100, which integrates at least one ambient light source configured to light the surface of the dental zone 50 with a second flux F'.

Accordingly, in this third example the ambient light source of the operating light can participate actively in obtaining the preferred value of the ratio E1/E2, whereas in the first and second embodiments the supplementary light sources enabled them to produce said preferred value of the ratio E1/E2 alone.

It indicates that all the other characteristics described in association with the first embodiment or the second embodiment, which have not been described again in association with the third embodiment to streamline the size of the present explanation, can evidently be reprises, by choice, alone or in combination, by this third embodiment.

In addition, it should be noted that the modes or embodiments described in the present explanation are given by way of illustration and non-limiting, where in terms of this explanation an expert can easily modify these modes or embodiments or envisage others within the scope of the invention.

Also, the different characteristics of these modes or embodiments can be used alone or can be combined. When they are combined, these characteristics can be as described hereinabove or different, as the invention is not limited to the specific combinations described in the present explanation. In particular, a characteristic described in relation to a mode or embodiment can be applied similarly to another mode or embodiment, unless specified otherwise.

The invention claimed is:
1. A dental lighting device, comprising at least one lighting system configured to light a predetermined dental zone with, over a first spectral range which is less than a reference wavelength, said reference wavelength being between 405 nm and 475 nm, a first average irradiance value E1 and, over a second spectral range greater than the reference wavelength, a second average irradiance value E2, and in which the lighting system is configured to function according to at least one first lighting mode, in which the ratio of the first average irradiance value E1 to the second average irradiance value E2 is less than 12, the lighting system being also configured to function according to at least one second lighting mode distinct from the first lighting mode, the dental lighting device comprising a switch configured to switch operation of the lighting system between the first lighting mode and the second lighting mode, and the switch being configured to switch operation of the lighting system between the first lighting mode and the second lighting mode by varying one of the two values of the first average irradiance value E1 and the second average irradiance value E2, whereas the other of these two values remains unchanged.

2. The device according to claim 1, in which the lighting system is configured, in the first lighting mode, to light the predetermined dental zone with the first average irradiance value E1 which is greater than 1 W/m$^2$.

3. The device according to claim 1, in which, in the first lighting mode, said ratio is greater than 1.

4. The device according to claim 1, in which, in the first lighting mode, said ratio is less than 10.

5. The device according to claim 1, in which the reference wavelength is between 440 nm and 460 nm.

6. The device according to claim 1, in which the first spectral range is between 370 nm and the reference wavelength.

7. The device according to claim 1, in which the second spectral range is between the reference wavelength and 780 nm.

8. The device according to claim 1, comprising an operating light, and in which the lighting system comprises at least one ambient light source connected to the operating light.

9. The device according to claim 1, comprising a supplementary instrument, and in which the lighting system comprises at least one supplementary light source connected to the supplementary instrument.

10. The device according to claim 9, in which the supplementary instrument comprises a body having a fixing part capable of cooperating with a tool to fix said tool and the body relative to each other, and at least one housing arranged in the region of the fixing part and in which said at least one supplementary light source is mounted.

11. The device according to claim 9, in which the lighting system comprises a plurality of discrete supplementary light sources.

12. The device according to claim 11, in which the lighting system comprises at least two supplementary light sources having separate emission spectra.

13. The device according to claim 11, in which the lighting system comprises a luminous flux mixer at the input of which luminous fluxes respectively emitted by the supplementary light sources are injected, and at the output of which a light beam (F) adapted to contribute in all or part to lighting the predetermined dental zone emerges, with the first average irradiance value E1 and the second average irradiance value E2.

14. The device according to claim 9, in which the supplementary light source comprises a light-emitting diode.

15. The device according to claim 1, in which the lighting system is configured so that the ratio of the first average irradiance value E1 to the second average irradiance value E2 has different values in the first lighting mode and in the second lighting mode respectively.

16. A process for lighting configuration using a dental lighting device, the dental lighting device comprising at least one lighting system configured to light a predetermined dental zone with, over a first spectral range which is less than a reference wavelength, said reference wavelength being between 405 nm and 475 nm, a first average irradiance value E1 and, over a second spectral range greater than the reference wavelength, a second average irradiance value E2, and in which the lighting system is configured to function according to at least one first lighting mode, in which the ratio of the first average irradiance value E1 to the second average irradiance value E2 is less than 12, the lighting system being also configured to function according to at least one second lighting mode distinct from the first lighting mode, the dental lighting device comprising a switch configured to switch operation of the lighting system between the first lighting mode and the second lighting mode, and the switch being configured to switch operation of the lighting system between the first lighting mode and the second lighting mode by varying one of the two values of the first average irradiance value E1 and the second average irradiance value E2, whereas the other of these two values remains unchanged, wherein the process comprises a configuration step of the lighting system, during which the lighting system is configured so that the latter operates according to the at least one first lighting mode, in which said lighting system lights the predetermined dental zone with, over the first spectral range which is less than the reference wavelength between 405 nm and 475 nm, the first average irradiance value E1 and, over the second spectral range greater than the reference wavelength, the second average irradiance value E2, and in which the ratio of the first average irradiance value E1 to the second average irradiance value E2 is less than 12, wherein the lighting system is configured by varying at least one of the first average irradiance value and the second average irradiance value.

\* \* \* \* \*